(12) United States Patent
Grisenti

(10) Patent No.: US 9,630,923 B2
(45) Date of Patent: Apr. 25, 2017

(54) BIOCATALYZED SYNTHESIS OF THE OPTICALLY PURE (R) AND (S) 3-METHYL-1,2,3,4-TETRAHYDROQUINOLINE AND THEIR USE AS CHIRAL SYNTHONS FOR THE PREPARATION OF THE ANTITHROMBIC (21R)- AND (21S)-ARGATROBAN

(71) Applicant: Euticals S.P.A., Milan (IT)

(72) Inventor: Paride Grisenti, Milan (IT)

(73) Assignee: EUTICALS SPA, Milan (IT)

( * ) Notice: Subject to any disclaimer, the term of this patent is extended or adjusted under 35 U.S.C. 154(b) by 0 days.

(21) Appl. No.: 14/992,226

(22) Filed: Jan. 11, 2016

(65) Prior Publication Data

US 2016/0122303 A1    May 5, 2016

Related U.S. Application Data

(63) Continuation of application No. PCT/EP2014/064307, filed on Jul. 4, 2014.

(30) Foreign Application Priority Data

Jul. 9, 2013  (EP) ..................................... 13175805

(51) Int. Cl.
| | | |
|---|---|---|
| *C07D 215/06* | (2006.01) | |
| *C12P 41/00* | (2006.01) | |
| *C12P 17/12* | (2006.01) | |
| *C12P 17/16* | (2006.01) | |

(52) U.S. Cl.
CPC ............ *C07D 215/06* (2013.01); *C12P 17/12* (2013.01); *C12P 17/165* (2013.01); *C12P 41/004* (2013.01)

(58) Field of Classification Search
CPC ...... C07D 215/06; C12P 41/004; C12P 14/12; C12P 14/165
See application file for complete search history.

(56) References Cited

U.S. PATENT DOCUMENTS 5,476,942 A    12/1995  Lassalle et al.

FOREIGN PATENT DOCUMENTS

JP    H07184685    7/1995

OTHER PUBLICATIONS

Ferraboschi, CA159:577494, abstract only of Tetrahedron: Asymmetry, vol. 24(18), 1142-1147, 2013.*
Brundish, et al., "Design and Synthesis of Thrombin Inhibitors: Analogues", J. Medicinal Chemistry, Amer. Chem. Soc., vol. 42, No. 22, Jan. 1, 1999, pp. 4584-4603.
Cossy, et al., "A short synthesis of argatroban", Bioorganic & Medicinal Chemistry Letters, vol. 11, No. 15, Aug. 1, 2001, pp. 1989-1992.
Alatorre-Santamaria, et al., "Stereoselective synthesis of optically active cyclic alpha- and beta-amino esters through lipase-catalyzed transesterification or interesterification processes", Tetrahedron Asymmetry, vol. 21, No. 18, Sep. 27, 2010, pp. 2307-2313.
Rawson, et al., "Separation of 21-(R)-Activity of the Individual Diastereomers", Journal of Pharmaceutical Sciences, vol. 82, No. 6, Jun. 1, 1993, pp. 672-673.
International Search Report issued in related application PCT/EP2014/064307 dated Nov. 11, 2014.

* cited by examiner

*Primary Examiner* — D M Seaman
(74) *Attorney, Agent, or Firm* — Stradley Ronon Stevens & Young, LLP

(57) ABSTRACT

The present invention relates to the biocatalyzed synthesis of enantiomerically pure (3R) and (3S)-methyl-1,2,3,4-tetrahydroquinoline. Said enantiomerically pure compounds are useful as chiral synthons in organic synthesis and, in particular, for the preparation of diastereomerically pure (21R) and (21S)-agratroban and its analogs. New compounds used as intermediates in the process of the invention are also disclosed.

20 Claims, No Drawings

BIOCATALYZED SYNTHESIS OF THE OPTICALLY PURE (R) AND (S) 3-METHYL-1,2,3,4-TETRAHYDROQUINOLINE AND THEIR USE AS CHIRAL SYNTHONS FOR THE PREPARATION OF THE ANTITHROMBIC (21R)- AND (21S)-ARGATROBAN

CROSS REFERENCE TO RELATED APPLICATIONS

This application is a continuation of International Application No. PCT/EP2014/064307 filed Jul. 4, 2014, and claims priority to European Patent Application No. 13175805.4 filed Jul. 9, 2013, the entire contents of each application are incorporated by reference herein, in their entirety and for all purposes.

FIELD OF THE INVENTION

The present invention refers to the field of biocatalyzed synthesis of organic compounds useful for the preparation of active agents. In particular, it refers to the synthesis of optically pure compounds useful as chiral synthons, in particular for the preparation of the antithrombotic compound argatroban.

BACKGROUND

Argatroban is an inhibitor of thrombin, the protease that plays a key role in the blood coagulation and fibrinolysis. (Stassen, J. M.; Arnout, J.; Deckmyn, H. Curr. Med. Chem., 2004, 11, 2245-2260. Sanderson, P. E. J.; NaylorOlsen, A. M. Curr. Med. Chem., 1998, 5, 289-304. Steinmetzer, T.; Sturzebecher, J. Curr. Med. Chem., 2004, 11, 2297-2321). The crucial role of thrombin in the coagulation cascade has made it a target for antithrombotic agents used in treatment of cardiovascular diseases (Abbenante, G.; Fairlie, D. P. Med. Chem. 2005, 1, 71-104). The most frequently prescribed anticoagulant with antithrombin activity is heparin, however limitations due to its chemical heterogeneity, in addition to several adverse events, as the heparin induced thrombocytopenia (HIT), prompted the development of low molecular weight selective inhibitors of thrombin. Argatroban (1; scheme 1) is a synthetic, small molecule that selectively and reversibly inhibits thrombin without generation of antibodies or degradation of proteases. (Yeh, R. W.; Jang, I K-K. Am. Heart J. 2006, 151, 1131-1138).

Scheme 1. Structural formula of Argatroban

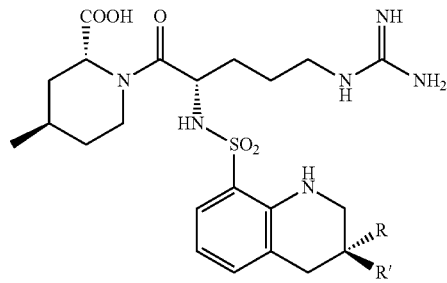

a. R = CH₃; R' = H (21R) Argatroban
b. R = H; R' = CH₃ (21S) Argatroban

After identification by Okamoto and co-worker (U.S. Pat. No. 4,258,192, Mitsubishi 1979) argatroban was introduced in Japan (Novastan®, MD-805), and later in Europe and in US for prophylaxis and treatment of thrombosis in patients with HIT (Moledina, M.; Chakir, M.; Gandhi, P. J. J. Thrombosis and Thrombolysis 2001, 12, 141-149). Three constituents are easily recognized in the chemical structure 1, the 4-methyl-2-piperidine carboxylic acid bonded to the arginine, in turn bonded to a 3-methyl-1,2,3,4-tetrahydroquinoline through a sulfonyl group. Four stereogenic centers are present in the structure three of which, with a mandatory configuration, introduced either with the aid of a chiral auxiliary and by the use of L-arginine among the starting materials. The stereocenter on the tetrahydroquinoline is introduced during the last step of the synthesis by reduction of the heteroaromatic ring of a quinoline that affords the (21R)- and (21S)-diastereoisomers (Cossy, J.; Belotti, D. Bioorg. Med. Chem. Lett. 2001, 11, 1989-1992).

The diastereoisomeric mixture is used as antithrombotic drug without separation of the (21R)- and (21S)-epimers (Scheme 1), 1a and 1b, respectively, provided that their ratio is 64/36±2. The 21R and 21S configurations have been assigned in 1993 by a X-ray study after the HPLC separation. (21S)-1b is twice as potent as (21R)-1a and about five times less soluble in water (Rawson, T. E.; VanGorp, K. A.; Yang, J.; Kogan, T. P. J. Pharm. Sci. 1993, 82, 672-673).

In order to characterize from a chemical physical point of view the two 21-epimers of argatroban 1 the present Inventor tried their separation by means of a fractional crystallization according to a published procedure (CN 100586946) but the obtained results were unsatisfactory from a preparative point of view.

Therefore, alternative methods for the preparation of enantiomerically pure (R)- and (S)-isomers of 3-methyl-1,2,3,4-tetrahydroquinoline (2), i.e. the suitable synthons for the preparation of (21R)- and (21S)-argatroban 1 (Scheme 2), are still needed.

Scheme 2. Structural formula of (21R)- and (21S)-argatroban (1) and its synthon 3-methyl-1,2,3,4-tetrahydroquinoline (2).

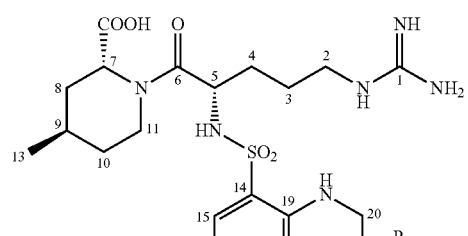

a. R = CH₃; R' = H (21R) Argatroban
b. R = H; R' = CH₃ (21S) Argatroban

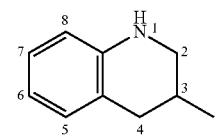

3-methyl-1,2,3,4-tetrahydroquinoline

Two synthesis of optically active 3-methyl-1,2,3,4-tetrahydroquinoline 2, both aimed at the preparation of argatroban 1 or its analogues are reported in literature: in one case the starting material is a tricyclic chiral auxiliary that, after acylation, in five steps leads to the optically pure (3R)-methyl-6-bromo-1,2,3,4-tetrahydroquinoline herein indicated also as (R,S)-6), a compound bearing a function convertible by a hydrolytic enzyme, is a suitable substrate for the obtainment of the optically pure chiral synthons (R) and (S)-6, immediate precursors of the (R) and (S) 3-methyl-1,2,3,4-tetrahydroquinoline (compounds (S)-2 and (R)-2) (Scheme 3).

Scheme 3. Synthesis of (3R)- and (3S)-methyl-1,2,3,4-quinoline.

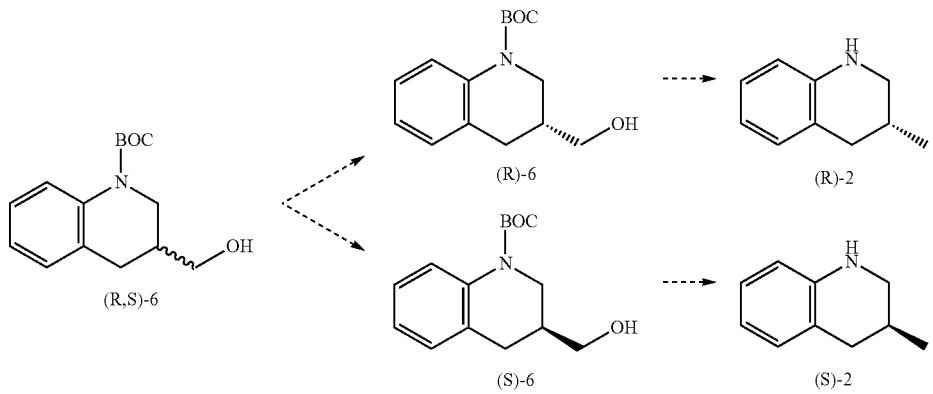

(Brundish, D.; Bull, A.; Donovan, V.; Fullerton, J. D.; Garman, S. M.; Hayler, J. F.; Janus, D.; Kane, P. D.; McDonnel, M.; Smith, G. P.; Wakeford, R.; Walker, C. V.; Howarth, G.; Hoyle, W.; Allen, M. C.; Ambler, J.; Butler, K.; Talbot, M. D. J. Med. Chem. 1999, 42, 4584-4603). The synthesis of (3S)-methyl-1,2,3,4-tetrahydroquinoline is described in a Synthelabo's patent: the starting material, in this case, is the optically pure methyl (R)-3-iodo-2-methylpropanoate (Lasalle, G.; Galtier, D.; Galli, F. 1995, U.S. Pat. No. 5,476,942). This synthesis presents very low overall yields.

However, a method for the preparation of both pure (3R)- and (3S)-methyl-1,2,3,4-tetrahydroquinoline starting from a common precursor and using the same reactant is not yet available.

An alternative method could be represented by a stereoselective catalytic hydrogenation of the suitable quinoline ring but it is reported that a chiral rhodium complex, giving optimal results (98% ee and quantitative yield) in the case of 2-substituted quinolines, failed the scope when applied to the 3-methylquinoline (Zhou, H.; Li, Z.; Wang, Z.; Wang, T.; Xu, L.; He, Y.; Fan, Q.-H; Pan, J.; Gu, L.; Chan, A. S. C. Angew. Chem. Int. Ed. 2008, 47, 8464-8467).

It has now been found an enzymatic approach for the synthesis of both enantiomerically pure (3R)- and (3S)-methyl-1,2,3,4-tetrahydroquinoline (compound 2).

SUMMARY OF THE INVENTION

Within the meanings of the present invention, by the term "enantiomerically pure" compound, it is intended an enantiomer of a compound having an enantiomeric excess (ee) of 99.0%.

The present invention uses an enzymatic approach to the synthesis of enantiomerically pure (3R)- and (3S)methyl-1,2,3,4-tetrahydroquinoline. The Applicant tested a number of enzymes, which, even if at a very low conversion extent, showed negligible ee values.

Surprisingly, it has been found that a racemic mixture of (R,S)-3-(1'-hydroxy-methyl)-1-tertbutyloxycarbonyl-1,2,3,4-tetrahydroquinoline (see Scheme 3 below, compound 6, It is therefore an object of the present invention a process for the preparation of enantiomerically pure isomers (R) and (S) of compound 3-methyl-1,2,3,4-tetrahydroquinoline, (R)-2 and (S)-2, respectively.

Referring to schemes A, B and C as general description and schemes 4, 5 and 6, reported as exemplary embodiments in the following detailed description, the present invention provides a process for the preparation of optically pure isomers (R) and (S) of compound 3-methyl-1,2,3,4-tetrahydroquinoline comprising the following steps:

a) transforming quinoline-3-carboxylic acid into the corresponding $C_1$-$C_4$ linear or branched alkyl or aryl ester, wherein aryl is a phenyl or benzyl moiety, optionally substituted with one or more $C_1$-$C_4$ linear or branched alkyl groups (R''' of scheme A);

b) reducing said ester to the corresponding (R,S)-1,2,3,4-tetrahydroquinoline-3-carboxylate ester;

c) reducing said (R,S)-1,2,3,4-tetrahydroquinoline-3-carboxylate ester to obtain (R,S)-3-(1'-hydroxy-methyl)-1,2,3,4-tetrahydroquinoline;

d) protecting the amino group of said (R,S)-3-(1'-hydroxy-methyl)-1,2,3,4-tetrahydroquinoline using di-tertbutyl carbonate to obtain (R,S)-3-(1'-hydroxy-methyl)-1-tertbutyloxycarbonyl-1,2,3,4-tetrahydroquinoline;

e) submitting the racemic mixture of (R,S)-3-(1'-hydroxy-methyl)-1-tertbutyloxycarbonyl-1,2,3,4-tetrahydroquinoline to a first transesterification catalyzed by Pseudomonas fluorescens lipase (PFL) in a toluenic solution using an ester of vinyl alcohol with a $C_2$-$C_8$, linear or branched alkyl carboxylic acid as acyl donor, wherein
the reaction is stopped at a PFL rate of conversion comprised between 30 and 40% to obtain isomer S of the corresponding (R,S)-3-(1'-carboalkoxy-methyl)-1-tertbutyloxycarbonyl-1,2,3,4-tetrahydroquinoline, which is subsequently hydrolyzed by PFL enzyme at a rate of conversion comprised between 60 and 75% to obtain the corresponding enantiomerically pure (S)-3-(1'-hydroxy-methyl)-1-tertbutyloxycarbonyl-1,2,3,4-tetrahydroquinoline,
or
the reaction is stopped at a PFL rate of conversion comprised between 55 and 65% in order to obtain the isomeric compound (R)-3-(1'-hydroxy-methyl)-1-tertbutyloxycarbonyl-1,2,3,4-tetrahydroquinoline in admixture with (S)-3-(1'-carboalkoxy-methyl)-1-tertbutyloxycarbonyl-1,2,3,4-tetrahydroquinoline, the former is subsequently submitted to a second PFL reaction at a conversion rate into the corresponding acylate comprised between 30 and 45% in order to obtain enantiomerically pure (R)-3-(1'-hydroxy-methyl)-1-tertbutyloxycarbonyl-1,2,3,4-tetrahydroquinoline;

f) transforming the obtained compound (R)- or (S)-3-(1'-hydroxy-methyl)-1-tertbutyloxycarbonyl-1,2,3,4-tetrahydroquinoline with a sulphonyl chloride R'''—SO$_2$—Cl, wherein R''' is a $C_1$-$C_4$ linear or branched alkyl, phenyl, optionally substituted by one or more methyl groups thus obtaining the corresponding sulphonyl derivative;

g) reducing said sulphonyl derivative to the corresponding (R)- or (S)-3-methyl-1-tertbutyloxycarbonyl-1,2,3,4-tetrahydroquinoline using a hydride;

h) removing the protective group of the amino nitrogen atom to obtain the corresponding, enantiomerically pure synthon (R)- or (S)-3-methyl-1,2,3,4-tetrahydroquinoline.

Accordingly, the present invention is characterized by a common starting compound, namely quinoline 3-carboxylic acid and common intermediates, namely the (R,S) 3-hydroxymethyl-1,2,3,4-tetrahydroquinoline, and its N—BOC-derivative.

Scheme A

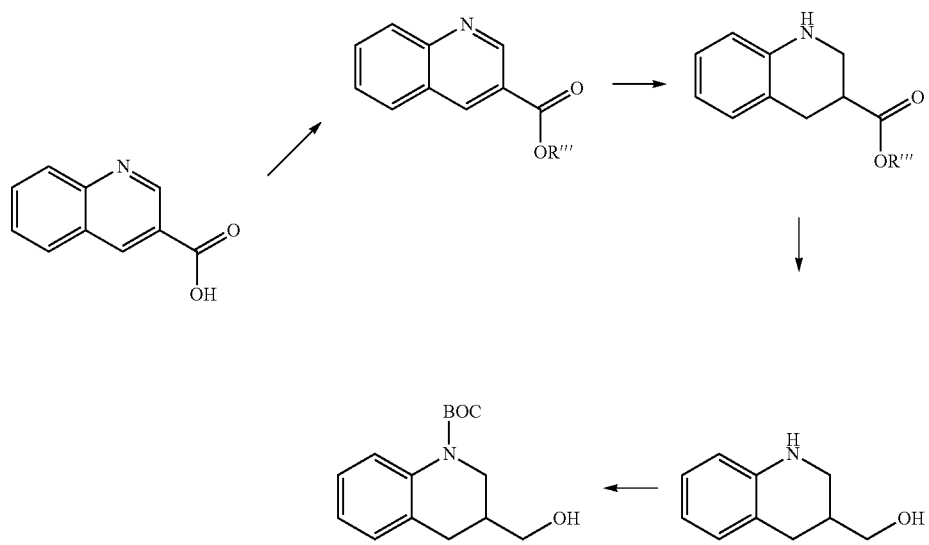

Scheme B

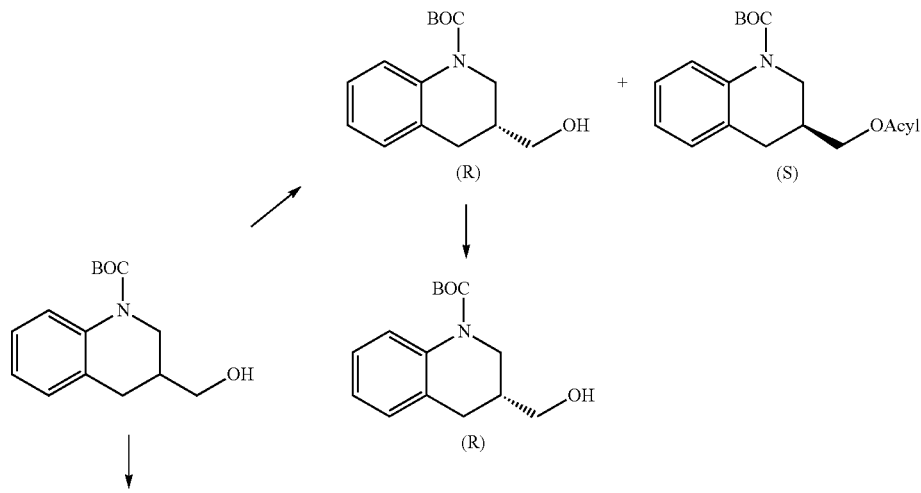

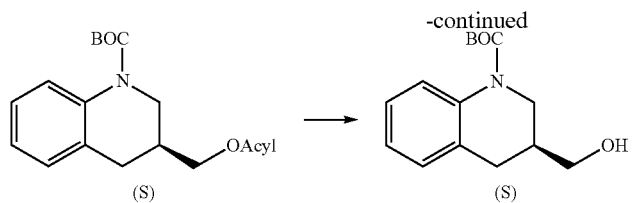

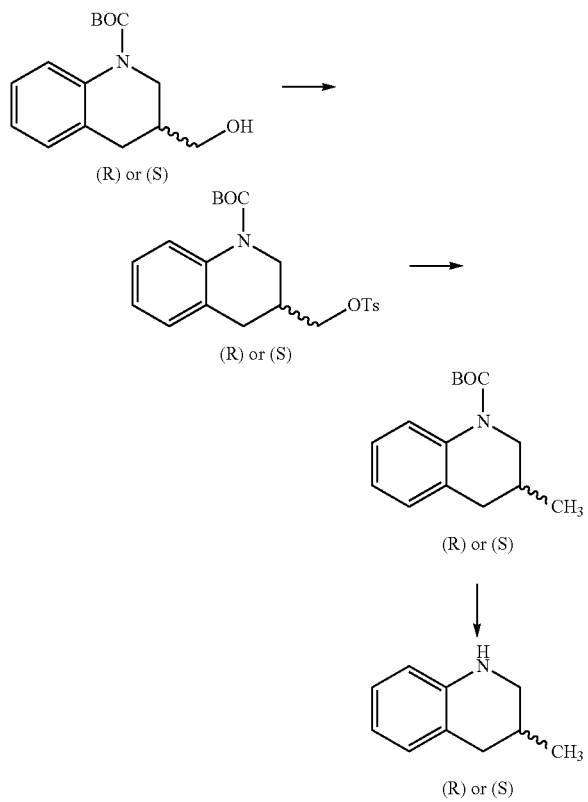

Scheme C

Therefore, it is an object of the present invention a process for the preparation of enantiomerically pure (3S)-methyl-1,2,3,4-tetrahydroquinoline comprising the following steps:
a) transforming quinoline-3-carboxylic acid into the corresponding $C_1$-$C_4$ linear or branched alkyl or aryl ester, wherein aryl is a phenyl or benzyl moiety, optionally substituted with one or more $C_1$-$C_4$ linear or branched alkyl groups;
b) reducing said ester to the corresponding (R,S)-1,2,3,4-tetrahydroquinoline-3-carboxylate ester;
c) reducing said (R,S)-1,2,3,4-tetrahydroquinoline-3-carboxylate ester to obtain (R,S)-3-(1'-hydroxy-methyl)-1,2,3,4-tetrahydroquinoline;
d) protecting the amino group of said (R,S)-3-(1'-hydroxy-methyl)-1,2,3,4-tetrahydroquinoline using di-tertbutyl carbonate to obtain (R,S)-3-(1'-hydroxy-methyl)-1-tertbutyloxycarbonyl-1,2,3,4-tetrahydroquinoline;
e) submitting the racemic mixture of (R,S)-3-(1'-hydroxy-methyl)-1-tertbutyloxycarbonyl-1,2,3,4-tetrahydroquinoline to a first transesterification catalyzed by *Pseudomonas fluorescens* lipase (PFL) in a toluenic solution using an ester of vinyl alcohol with a $C_2$-$C_8$, linear or branched alkyl carboxylic acid as acyl donor, wherein the reaction is stopped at a PFL rate of conversion comprised between 30 and 45% to obtain isomer S of the corresponding (R,S)-3-(1'-carboalkoxymethyl)-1-tertbutyloxycarbonyl-1,2,3,4-tetrahydroquinolin, which is subsequently hydrolyzed by PFL enzyme at a rate of conversion comprised between 60 and 75% to obtain the corresponding enantiomerically pure (S)-3-(1'-hydroxy-methyl)-1-tertbutyloxycarbonyl-1,2,3,4-tetrahydroquinoline;
f) transforming the obtained compound (S)-3-(1'-hydroxy-methyl)-1-tertbutyloxycarbonyl-1,2,3,4-tetrahydroquinoline with a sulphonyl chloride R"—$SO_2$—Cl, wherein R" is a $C_1$-$C_4$ linear or branched alkyl, phenyl, optionally substituted by one or more methyl groups thus obtaining the corresponding sulphonyl derivative;
g) reducing said sulphonyl derivative to the corresponding (S)-3-methyl-1-tertbutyloxycarbonyl-1,2,3,4-tetrahydroquinoline using a hydride;
h) removing the protective group of the amino nitrogen atom to obtain the corresponding, enantiomerically pure synthon (S)-3-methyl-1,2,3,4-tetrahydroquinoline.

It is another object of the present invention a process for the preparation of enantiomerically pure (3R)-methyl-1,2,3,4-tetrahydroquinoline comprising the following steps:
a) transforming quinoline-3-carboxylic acid into the corresponding $C_1$-$C_4$ linear or branched alkyl or aryl ester, wherein aryl is a phenyl or benzyl moiety, optionally substituted with one or more $C_1$-$C_4$ linear or branched alkyl groups;
b) reducing said ester to the corresponding (R,S)-1,2,3,4-tetrahydroquinoline-3-carboxylate ester;
c) reducing said (R,S)-1,2,3,4-tetrahydroquinoline-3-carboxylate ester to obtain (R,S)-3-(1'-hydroxy-methyl)-1,2,3,4-tetrahydroquinoline;
d) protecting the amino group of said (R,S)-3-(1'-hydroxy-methyl)-1,2,3,4-tetrahydroquinoline using di-tertbutyl carbonate to obtain (R,S)-3-(1'-hydroxy-methyl)-1-tertbutyloxycarbonyl-1,2,3,4-tetrahydroquinoline;
e) submitting the racemic mixture of (R,S)-3-(1'-hydroxy-methyl)-1-tertbutyloxycarbonyl-1,2,3,4-tetrahydroquinoline to a first transesterification catalyzed by *Pseudomonas fluorescens* lipase (PFL) in a toluenic solution using an ester of vinyl alcohol with a $C_2$-$C_8$, linear or branched alkyl carboxylic acid as acyl donor, wherein the reaction is stopped at a PFL rate of conversion comprised between 55 and 65% in order to obtain the isomeric compound (R)-3-(1'-hydroxy-methyl)-1-tertbutyloxycarbonyl-1,2,3,4-tetrahydroquinoline in admixture with (S)-3-(1'-carboalkoxymethyl)-1-tertbutyloxycarbonyl-1,2,3,4-tetrahydroquinoline, the former is subsequently submitted to a second PFL reaction at a conversion rate into the corresponding acylate comprised between 30 and 45% in order to obtain enantiomerically pure (R)-3-(1'-hydroxy-methyl)-1-tertbutyloxycarbonyl-1,2,3,4-tetrahydroquinoline;

f) transforming the obtained compound (R)-3-(1'-hydroxy-methyl)-1-tertbutyloxycarbonyl-1,2,3,4-tetrahydroquinoline with a sulphonyl chloride R"—SO$_2$—Cl, wherein R" is a C$_1$-C$_4$ linear or branched alkyl, phenyl, optionally substituted by one or more methyl groups thus obtaining the corresponding sulphonyl derivative;

g) reducing said sulphonyl derivative to the corresponding (R)-3-methyl-1-tertbutyloxycarbonyl-1,2,3,4-tetrahydroquinoline using a hydride;

h) removing the protective group of the amino nitrogen atom to obtain the corresponding, enantiomerically pure synthon (R)-3-methyl-1,2,3,4-tetrahydroquinoline.

It is also an object of the present invention the compound 3R-methyl-1,2,3,4-tetrahydroquinoline (herein indicated as (R)-2) having the following structural formula (I),

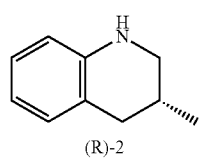

(I)

(R)-2

The use of said compound (R)-2, as well as the corresponding enantiomer (S)-2 as chiral synthons, in particular for the preparation of (21R)- and (21S)-argatroban (compound 1), respectively is also within the scope of the present invention.

Compounds (R)-3-(1'-hydroxy-methyl)-1-tertbutyloxycarbonyl-1,2,3,4-tetrahydroquinoline; (S)-3-(1'-hydroxy-methyl)-1-tertbutyloxycarbonyl-1,2,3,4-tetrahydroquinoline; (S)-3-(1'-hydroxymethyl-acetate)-1-tertbutyloxycarbonyl-1,2,3,4-tetrahydroquinoline; (S)-3-(1'-sulphonyloxy-methyl)-1-tertbutyloxycarbonyl-1,2,3,4-tetrahydroquinoline; (R)-3-(1'-sulphonyloxy-methyl)-1-tertbutyloxycarbonyl-1,2,3,4-tetrahydroquinoline are novel intermediates in the process above described, therefore are also objects of the present invention. Also their use as chiral synthons in organic synthesis is an object of the present invention.

The new chemoenzymatic approach of the present invention has the following main advantages:

possibility to easily prepare optically pure (R) and (S) 3-methyl-1,2,3,4 tetrahydroquinoline (compounds (S)-2 and (R)-2), the chiral synthons for the preparation of diastereomerically pure 21-(R) and 21-(S) argatroban;

access to new diastereomerically pure argatroban analogues.

In fact optically pure (R) 3-methyl-1,2,3,4-tetrahydroquinoline-8-sulphonic acid and the respective chloride, that can be prepared from compound (R)-2 provided by the present invention, following described methods (for example U.S. Pat. No. 5,476,942), is the starting material for several modified analogues of Argatroban (Brundish, D.; Bull, A.; Donovan, V.; Fullerton, J. D.; Garman, S. M.; Hayler, J. F.; Janus, D.; Kane, P. D.; McDonnel, M.; Smith, G. P.; Wakeford, R.; Walker, C. V.; Howarth, G.; Hoyle, W.; Allen, M. C.; Ambler, J.; Butler, K.; Talbot, M. D. J. Med. Chem. 1999, 42, 4584-4603) modified in the arginine or in the piperidyl moiety, prepared in attempts to develop drugs with increased efficacy and bioavailability.

Moreover, and it is an object of the present invention, (R)-3-(1'-hydroxy-methyl)-1-tertbutyloxycarbonyl-1,2,3,4-tetrahydroquinoline and (S)-3-(1'-hydroxy-methyl)-1-tertbutyloxycarbonyl-1,2,3,4-tetrahydroquinoline can be useful in order to obtain the farnesyl protein transferase inhibitors reported in U.S. Pat. No. 6,362,188, avoiding the separation by a preparative HPLC of the imidazolyl intermediate (see steps B-F, column 125-127 of the above cited patent).

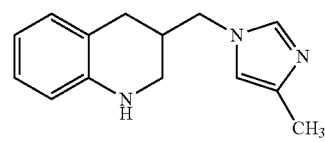 [SMILES: Cc1cn(CC2CNc3ccccc3C2)cn1]

DETAILED DESCRIPTION OF THE INVENTION

The present invention is now disclosed in detail, through an exemplary embodiment shown in the following Schemes 4, 5 and 6, being intended that variations of the materials, conditions and parameters within the boundaries defined in the independent claims are comprised in the present invention.

By referring to exemplary Scheme 4, below, which illustrates an exemplary embodiment of the present invention, starting from an ester as defined in the above Summary of the Invention, for example a methyl ester (compound 4) of commercially available 3-quinoline carboxylic acid, 3-carboxymethyl-1,2,3,4-tetrahydroquinoline is prepared (compound 5) (78% from 3-carboxylic acid) by suitable reduction, for example selective hydrogenation with sodium cyanoborohydride, as described by Gotor et al. (Alatorre-Santamaria, S.; Gotor-Fernandez, V.; Gotor, V. Tetrahedron: Asymmetry 2010, 21, 2307-2313). Other suitable reagents that can be used to carry out this reaction include also the catalytic hydrogenation over palladium dioxide in methanol (Nagata, R.; Tanno, N.; Kodo, T.; Ae, N.; Yamaguchi, H.; Nishimura, T.; Antochu, F; Tatsuno, T.; Kato, T.; Tanaka, Y.; Nakamura, M.; J. Med. Chem. 1994, 37, 3956-3968). Subsequently, the ester group of compound 5 is reduced to primary alcohol with conventional methods, for example with a metal hydride, preferably LiAlH$_4$ affording the 3-hydroxymethyl derivative (compound 3) (89%).

Scheme 4

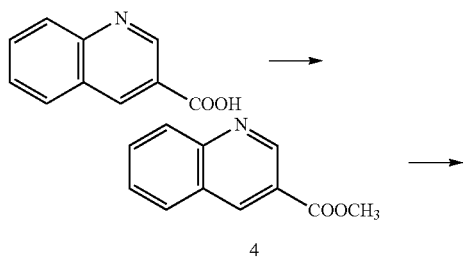

4

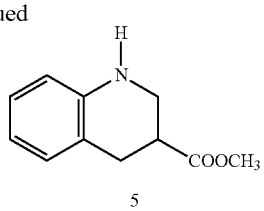

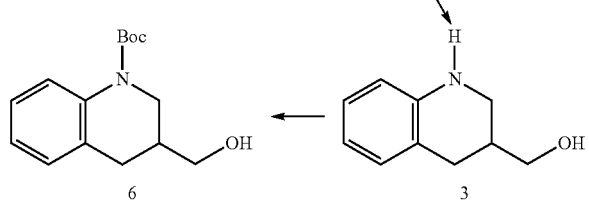

as a racemic mixture (Guzi, T.; Rane, D. F.; Mallams, A. K.; Cooper, A. B.; Doll, R. J.; Girijavallabhan, V. M.; Taveras, A. G.; Strickland, C.; Kelly, J. M.; Chao, J. 2002, U.S. Pat. No. 6,362,188), is transformed into known chiral synthon (S) 2 by esterification to tosylate 8, lithium aluminum hydride reduction and removal of protecting group (59% yield from 6); in the Scheme 6 below, the same synthetic sequence above described for the (S) (+) acetate 7 isomer is detailed for the (R) isomer.

After protection of the amino group (80% yield), with tert-butyl carbonate, the so obtained tert-butyl carbamate (compound 6) is used for the transesterification with *Pesudomonas fluorescens* lipase (PFL).

By reference to exemplary Scheme 5, the racemic mixture of (R,S)-3-(1'-hydroxy-methyl)-1-tertbutyloxycarbonyl-1,2,3,4-tetrahydroquinoline (6) is submitted to a first transesterification catalyzed by (PFL) in a toluenic solution using an ester of vinyl alcohol with a $C_2$-$C_8$, linear or branched alkyl carboxylic as acyl donor, acetyl being the preferred acyl group. The reaction is stopped at a PFL rate of conversion comprised between 30 and 40% to obtain isomer S of the corresponding 1'-acylate, (R,S)-3-(1'-carboalkoxymethyl)-1-tertbutyloxycarbonyl-1,2,3,4-tetrahydroquinoline ((S)-7).

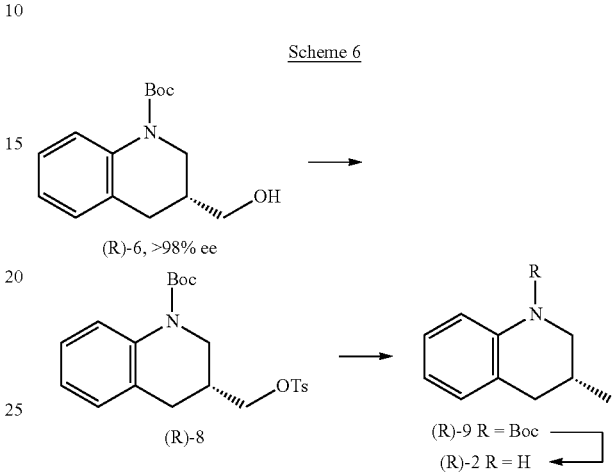

By comparison of the optical rotation of 2 with the reported one (U.S. Pat. No. 5,476,942) the S configuration is assigned to 3-methyl-1,2,3,4-tetrahydroquinoline obtained starting from (+)-acetate 7. The optical purity of 2, determined by chiral HPLC, shows that the ee of alcohol 6 is kept unaltered in the course of the synthesis.

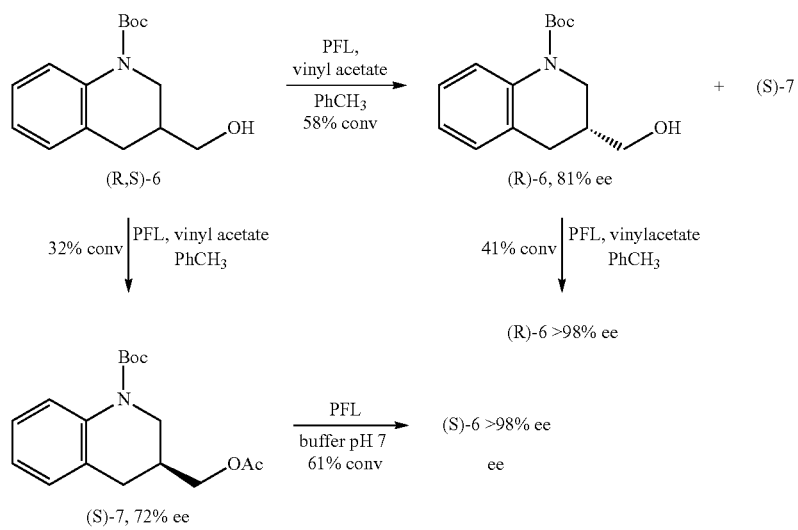

Enantiomerically enriched (+)-acetate 7 is then submitted to a further PFL-catalyzed hydrolysis. The reaction can be monitored by GLC and stopped at rate of conversion comprised between 60 and 75%. The obtained alcohol 6 is enantiomerically pure (≥99.0% ee) (determined by chiral HPLC). In order to establish the stereochemical outcome of the double resolution, alcohol 6, reported in literature only In order to obtain (R)-3-methyl-1,2,3,4-tetrahydroquinoline 2, corresponding to (R)-6 (i.e. the slower reacting enantiomer in the course of the PFL-catalyzed transformation) the PFL-catalyzed transesterification is stopped at 55-65%, for example 58%, conversion rate and the ee of obtained (+)-6 is determined, after acetylation, by HPLC on chiral column. Since the moderate obtained ee (81%), according to the present invention, enriched (R)-6 is submitted to a second PFL-catalyzed transesterification as a "continuation" of the first resolution. The desired ≥99.0% ee of (R)-6 is achieved stopping the reaction at 30-45%, for example 41% conversion rate (Scheme 5). Following the same synthetic pathway previously optimized for (S)-2, also (R)-2 is then available as chiral building block for the synthesis of (R)- and (S)-1,2,3,4-tetrahydroquinoline sulfonic acid chloride according to a known method (U.S. Pat. No. 5,476,942).

To the best of Applicant's knowledge, optically pure (R) and (S) isomers of compounds 3, 6, 7 and 8 as well as the compound (R)-2 are herein disclosed for the first time and fully characterized.

Referring to step a) of the process of the present invention, the synthetic step from quinoline-3-carboxylic acid to compound 4 can be carried out according to methods well-known to the skilled person, for example using thionyl chloride as reagent in methanolic solution in a temperature range comprised between 30 and 65° C., preferably at 65° C. According to a preferred embodiment for the methyl ester, the reaction is carried out using methanol as unique solvent at a concentration of the quinoline 3-carboxylic acid comprised between 0.10 and 0.005 M, preferably 0.05M and the relative molar ratio between thionyl chloride and quinoline-3-carboxylic acid is comprised in a range of 1:4 to 1:2, preferably 1:3.

The synthetic step b), from compound 4 to compound 5, namely a reduction, is also part of the general common knowledge. In a preferred embodiment of the present invention, this step is carried out in a solvent mixture of polar protic and aprotic solvents and using as reducing agent sodium cyanoborohydride in a pH range comprised between 3 and 5, preferably 4, in a temperature range comprised between 15 and 30° C., preferably 25° C. According to a preferred embodiment the polar protic solvent is methanol and the aprotic polar solvent is tetrahydrofuran in relative volumetric ratio comprised between 0.3 and 0.5, preferably 0.47; the concentration of compound 4 is comprised in a range of 0.1-0.3M, preferably 0.2M; the relative molar ratio between sodium cyanoborohydride and compound 4 is comprised in a range of 3.5-5.0. preferably 4.2 and the pH range is corrected by addition of a 4M hydrochloric acid solution in an aprotic solvent, preferably 1,4-dioxane or tetrahydrofuran.

The synthetic step c) from compound 5 to compound 3 is also well known in the art and can be, for example, carried out in a polar aprotic solvent using as reducing agent a typical hydride, for example lithium aluminum hydride, in a temperature range comprised between 15 and 30° C., preferably at 25° C. According to a preferred embodiment the polar aprotic solvent is tetrahydrofuran; the concentration of compound 5 is comprised in the range 0.10-0.20 M, preferably 0.14 M; the relative molar ratio between lithium aluminum hydride and compound 5 is comprised in a range of 3.5-5.0. preferably 4.

The synthetic step d) from compound 3 to compound 6 is carried out in a mixture of water and a polar water miscible organic solvent and using di-tertbutyl carbonate as reagent in the presence of an inorganic base in a temperature range comprised between 15 and 30° C., preferably 25° C. According to a preferred embodiment the polar water miscible solvent is 1,4 dioxane; the relative volumetric ratio between 1,4 dioxane and water is comprised between 0.7 and 0.9, preferably 0.8; the concentration of compound 3 in the reaction mixture is comprised in a range of 0.005-0.10M, preferably 0.05M; the relative molar ratio between sodium hydroxide and compound 3 is comprised in a range between 10 and 13, preferably 11.5; the relative molar ratio between sodium di-terbutyl carbonate and compound 3 is comprised in a range between 9.0 and 11.0. preferably 10.4.

The synthetic step from compound 6 to compound 7, performed in order to obtain an analytical standard of (R,S-7), is carried out in the presence of an organic base and using as acylating agent acetic anhydride or acetyl chloride in a temperature range comprised between 15 and 30° C., preferably 25° C.

According to a preferred embodiment the organic base is pyridine or triethylamine also used as solvent of reaction; the acylating agent is acetic anhydride and the concentration of compound 6 is comprised in a range between 0.30-0.42M, preferably 0.34 M; the relative molar ratio between acetic anhydride and compound 6 is comprised in a range between 3.0 and 4.0, preferably 3.5.

The synthetic step e) from compound (R,S)-6 to compound (R)-6 is carried out in two consecutive enzymatic steps in toluenic solution using a vinyl ester, preferably acetyl ester, as acyl donor and PFL as enzyme in a temperature range comprised between 15 and 30° C., preferably 25° C.

According to a preferred embodiment the concentration of compound (R,S)-6 in the reaction mixture is comprised in a range between 0.03-0.05M, preferably 0.04M; the relative molar ratio between vinyl ester and compound (R,S)-6 is comprised in a range between 3.8 and 4.6, preferably 4.2; the relative ratio between the enzymatic units of PFL and the mmoles of compound (R,S)-6 is comprised in a range between 200 and 300 U/mmol, preferably 210 U/mmol, and the vinyl ester is vinyl acetate, vinyl propionate or vinyl butyrate. In order to obtain optically pure compound (R)-6 the rate of conversion of the first enzymatic step has to be comprised between 55 and 65%, preferably 60%, into the corresponding acetate 7 and the second step at 30-40% of conversion into the corresponding acetate 7.

The synthetic step from compound (R,S)-6 to compound (S)-6 is carried out in two consecutive enzymatic steps, the first step is carried out in the same experimental conditions already described for compound (R)-6 but the reaction is stopped at a rate of conversion comprised between 30-40%, preferably 35%. Compound 7 recovered from the first enzymatic step is then enzymatically hydrolyzed at 20-25° C. in water solution using PFL as enzyme: this second enzymatic reaction is stopped at a rate of conversion comprised between 65-75%, preferably 70%, into the corresponding (S)-6 alcohol. According to a preferred embodiment the concentration of compound 7 in water is comprised in a range comprised between 0.03-0.10M, preferably 0.06M and the pH value comprised between 6.5 and 7.5, preferably 7.0; the relative ratio between the enzymatic units of the PFL and the mmoles of compound (S)-7 is comprised in a range between 220 and 260 U/mmol, preferably 240 U/mmol. The above indicate pH range can be reached using a 0.10-0.40 M phosphate buffer, preferably a 0.2M phosphate buffer.

Typically, the synthetic step from compound (R)-6 to compound (R)-8 is realized in the presence of an organic base using a sulphonyl chloride, for example tosyl chloride, as reagent in a temperature range comprised between 20 and 30° C., preferably at 25° C. In a preferred embodiment the organic base is pyridine or triethylamine, the relative molar ratio between exemplary tosyl chloride and compound (R)-6 is comprised between 1 and 3, preferably 2, and the concentration of compound (R)-6 in the reaction mixture is comprised between 2.0 and 1.0M, preferably 1.5M.

The synthetic step from compound (R)-8 to compound (R)-9 is also well-known in the art and can be carried out, for example, using as reducing agent a hydride in an aprotic organic solvent in a temperature range comprised between 20 and 25° C. In a preferred embodiment the hydride is lithium aluminum hydride and the aprotic solvent is tetrahydrofuran; the concentration of compound (R)-8 in the reaction mixture is comprised in a range of 0.10-0.20M, preferably 1.5M, and the relative molar ratio between compound (R)-8 and lithium aluminum hydride is comprised in a range of 0.20-0.30. preferably 0.25.

The synthetic step from compound (R)-9 to compound (R)-2 is carried out according to the general common knowledge, for example in the presence of a strong acid in an aprotic organic solvent in a temperature range comprised between 15 and 25° C. In a preferred embodiment the strong acid is trifluoroacetic acid or hydrochloric acid and the organic solvent is dichloromethane, 1,4 dioxane or tetrahydrofuran; the concentration of compound (R)-9 in the reaction mixture is comprised between 0.30 and 0.50M, preferably 0.35M, and the concentration of the acid in the reaction mixture is comprised in a range of 1.5-2.5M, preferably 2.0M.

The present invention will be now described more in detail by the following non limiting examples.

EXAMPLES

Materials and Methods

All the reagents and enzymes were purchased by Sigma-Aldrich. CAL B CLEA was purchased by CLEA Technologies (Netherland). All reactions were monitored by TLC on silica gel 60 $F_{254}$ precoated plates with a fluorescent indicator (Merck) with detection by spraying with a 10% phosphomolybdic acid ethanol solution and heating at 110° C. Column chromatographies were performed on silica gel 60 (70-230 mesh) (Merck) with a substrate/silica gel ratio 1:20. HPLC analyses were performed with a Merck-Hitachi L-6200; chiral column: Phenomenex Lux 3μ Cellulose-1, 250×4.6 mm; UV detector wavelength 254 nm). GLC analyses are performed with a Hewlett-Packard 5890-series II. $^1$H-NMR spectra were recorded on a Bruker-Avance 500 MHz spectrometer. $^{13}$C NMR spectra were collected at 125.76 MHz. The values of optical rotations were registered on a Perkin-Elmer (mod. 343) polarimeter in a 1 dm cell at 20° C., setting the wavelength at 589 nm. Mass spectra were recorded on a Agilent instrument (mod 6339 Ion trap LC/MS) using the ESI source with positive ion polarity; the samples were dissolved in methanol (0.02 μg μl$^{-1}$) and were examined utilizing the direct inlet probe technique at an infusion rate of about 0.6 mL min$^{-1}$; data acquisition and analysis were accomplished with Bruker Daltonics Data Analysis 3.3 software. The infrared spectra were registered on a Perkin Elmer instrument (mod. FT-IR spectrum one) equipped with universal attenuated total reflection (ATR) sampling.

When cited, the term "usual work-up" includes anhydrification of the organic phase with conventional methods, for example anhydrous sodium sulphate, filtration and removal of the solvent, for example by vacuum evaporation.

Example 1

Preparation of Methyl quinoline-3-carboxylate (compound 4)

Quinoline-3-carboxylic acid (8 g, 46.2 mmol) was dissolved in methanol (900 mL); thionyl chloride (5 mL, 68.5 mmol) was added at 0° C. The solution was kept at reflux, under stirring (10 h), monitoring the reaction progress by TLC (dichloromethane/methanol 9:1). An additional amount of thionyl chloride (5 mL) was added and the solution was kept at reflux (20 h). After cooling at room temperature, the solvent was evaporated at reduced pressure. To the residue, water (400 ml) and 1M sodium hydroxide (until pH 8) were added; the mixture was extracted with dichloromethane (4×400 mL). The collected organic phases were dried over sodium sulfate; after filtration, the solvent was removed at reduced pressure, affording title compound 4 (7.78 g, 89%) directly used in the next step without any further purification. The chemical-physical properties are in agreement with the reported ones (Alatorre-Santamaria, S.; Gotor-Fernández, V.; Gotor, V. Tetrahedron: Asymmetry 2010, 21, 2307-2313).

Example 2

Preparation of (R,S)-Methyl 1,2,3,4-tetrahydroquinoline-3-carboxylate (compound 5)

To a solution of methyl ester 4 (7.68 g, 41 mmol) in dry tetrahydrofuran (150 mL) and methanol (70 mL) sodium cyanoborohydride (10.8 g, 172 mmol) was added, under nitrogen atmosphere. The pH was adjusted at 4, by addition of 4M hydrogen chloride in dioxane and kept at this value, in the course of the reaction (10 h), by addition of the same hydrogen chloride solution. The reaction progress was monitored by TLC (dichloromethane/acetone 9:1) until the starting material disappearance. The reaction mixture was cooled in an ice bath, water (200 ml) and a saturated sodium hydrogen carbonate aqueous solution (until neutral pH) were added. Organic solvents were removed at reduced pressure. The aqueous phase was extracted with ethyl acetate (3×200 mL). The collected organic phases are dried over sodium sulfate and after usual work-up an oily residue (8.84 g) was obtained; the residue was purified by silica gel column chromatography: by elution with hexane/ethyl acetate (9:1) pure 5 was recovered (6.88 g, 88%). The chemical-physical properties are in agreement with the reported ones (Alatorre-Santamaría, S.; Gotor-Fernández, V.; Gotor, V. Tetrahedron: Asymmetry 2010, 21, 2307-2313).

Example 3

Preparation of (R,S)-3-(1'-hydroxy-methyl)-1,2,3,4-tetrahydroquinoline (compound 3)

To a suspension of lithium aluminum hydride (5.3 g, 140 mmol) in dry tetrahydrofuran (125 mL), cooled at 0-5° C., ester 5 (6.68 g, 35 mmol), dissolved in tetrahydrofuran (125 mL) was added dropwise. The ice bath was then removed and the reaction mixture was kept at room temperature (4 h), monitoring the reaction progress by TLC (dichloromethane/acetone 9:1) until starting material disappearance. To the reaction mixture, cooled at 0-5° C., water (5.3 mL), 15% sodium hydroxide aqueous solution (5.3 mL) and water (16 mL) were sequentially added. The white precipitate was removed by suction through a Celite pad. The solvent was evaporated at reduced pressure and the recovered oily 3 (5.02 g, 89%) was used in the next step without any further purification.

$^1$H NMR (CDCl$_3$) δ 2.23 (m, 1H, H-3); 2.56 (dd, 1H, H-4); 2.88 (dd, H-4); 2.62-2.82 (m, 2H, exchange with D$_2$O); 3.15 (dd, 1H, H-2); 3.46 (ddd, 1H, H-2); 3.64 (dd, 1H, H-1'); 3.72 (dd, 1H, H-1'); 6.53 (d, 1H, H-5); 6.67 (dd, 1H, H-6); 6.97-7.05 (m, 2H, H-7 and H-8).

IR $v_{max}$ 3380.86, 3238.16, 2918.32, 2864.52, 2837.38, 1602.37, 1582.56, 1494.88, 1471.35, 1368.95, 1323.05, 1293.83, 1266.81, 1071.36, 1022.97 cm$^{-1}$ MS (ESI+) m/z 164.1 [M+1]$^+$, 186.0 [M+Na]$^+$, 375 [2M+2Na]$^+$.

Example 4

Preparation of (R,S)-3-(1'-hydroxy-methyl)-1-tert-butyloxycarbonyl-1,2,3,4-tetrahydroquinoline (compound 6)

To a solution of 3 (4.90 g, 30 mmol) in dioxane (230 mL) and water (290 mL) sodium hydroxide (14 g, 0.35 mol) and di-tertbutyl carbonate (72 mL, 313 mmol) were sequentially added. The reaction mixture was kept, under stirring, at room temperature (24 h). The reaction progress was monitored by TLC (dichloromethane/methanol 9:1). The dioxane was removed at reduced pressure and the remaining aqueous phase was extracted with dichloromethane (4×70 mL). The collected organic phases were washed with water (2×100 mL) until pH 7. After usual work-up a yellow oil was obtained that was purified by silica gel column chromatography. Desired Boc derivative 6 (6.3 g, 80%) was recovered by elution with hexane/ethyl acetate 8:2. $^1$H-NMR (CDCl$_3$) δ 1.54 (s, 9H, CH$_3$); 1.89 (br s, 1H, exchange with D$_2$O); 2.31 (m, 1H, H-3); 2.53 (dd, 1H, H-4); 2.99 (dd, 1H, H-4); 3.50 (dd, 1H, H-2); 3.57-3.65 (m, 2H, H-2 and H-1'); 3.92 (dd, 1H, H-1'); 7.04 (dd, 1H, H-6); 7.11 (d, 1H, H-5); 7.16 (dd, 1H, H-7); 7.59 (d, 1H, H-8).

IR $v_{max}$ 3430.76, 2975.98, 2929.84, 1690.36, 1673.95, 1492.20, 1367.09, 1159.36 cm$^{-1}$ MS (ESI+) m/z 286.1 [M+Na]$^+$, 549.1 [2M+Na]$^+$.

Example 5

Preparation of (R,S)-3-(1'-hydroxy-methyl)-1-tert-butyloxycarbonyl-1,2,3,4-tetrahydroquinoline, 1'-acetate (compound 7)

To a solution of (R,S)-6 (0.200 g, 0.76 mmol) in dry pyridine (2 mL) acetic anhydride (0.25 mL, 2.64 mmol) was added. The reaction mixture was kept at room temperature overnight. The TLC analysis (hexane/ethyl acetate 7:3) showed a complete conversion. The solution was poured in ice cooled water (40 mL) and the product was recovered by extraction with dichloromethane (3×40 mL). The collected organic phases were washed with water (3×40 mL). After usual work-up crude acetate 7 was recovered. Purification on silica gel column chromatography (hexane/ethyl acetate 9:1 as eluant) afforded pure 7 (0.204 g, 88%). $^1$H NMR (CDCl$_3$) δ 1.55 (s, 9H, (CH$_3$)$_3$C); 2.11 (s, δ 3H, CH$_3$CO); 2.37 (m, 1H, H-3); 2.58 (dd, 1H, H-4); 2.93 (dd, 1H, J=16.02 and 5.65 Hz, H-4); 3.37 (dd, 1H, H-2); 3.96-4.16 (m, 3H, 2H-1' and H-2); 7.02 (dd, 1H, H-6); 7.11 (d, 1H, H-5); 7.17 (dd, 1H, H-7); 7.65 (d, 1H, H-8).

IR $v_{max}$ 2976.11, 2932.21, 1741.73, 1697.36, 1492.67, 1367.59, 1239.61, 1161.70 cm$^{-1}$ MS (ESI+) m/z 328.2 [M+Na]$^+$, 344 [M+K]$^+$.

Example 6

Isolation of (R)-3-(1'-hydroxy-methyl)-1-tertbutyloxycarbonyl-1,2,3,4-tetrahydroquinoline (compound (R)-6)

First Resolution

To a solution of (R,S)-6 (1.95 g, 7.4 mmol) in toluene (168 mL) vinyl acetate (2.93 ml, 31.4 mmol) and PFL (36 mg, 40.2 U/mg) were sequentially added. The reaction mixture was kept at room temperature, under vigorous stirring in a screw cap flask. The reaction progress was monitored by GLC (column: HP-5 WB, 30 m, 0.88 µm, ID 0.53 mm; oven temperature: 160° C., isothermal; carrier N$_2$; 140 kPa). R$_t$ Alcohol 6 9.8 min; acetate 7 15.5 min. The reaction was stopped at 58% conversion; the enzyme was removed by filtration and the solvent was evaporated at reduced pressure. The residue (1.91 g) was purified by silica gel column chromatography. By elution with hexane/ethyl acetate 9:1 acetate 7 was recovered (1.02 g, 45%). Elution with hexane/ethyl acetate 7:3 afforded alcohol 6 (0.69 g, 35%). The ee of (R)-6 (81%) was determined, after acetylation (acetic anhydride in pyridine) by HPLC analysis on chiral stationary phase (eluant: n-hexane/2-propanol 100:2; flow rate 0.250 mL min$^{-1}$), by comparison with the chromatogram of racemic acetate 7. R$_t$ (S)-7 48.72; (R)-7 52.34. The acetylation was required in order to suitably separate (R)- and (S)-isomers.

Second Resolution

To a solution of 6 (81% ee, 0.600 g, 2.28 mmol), obtained from the first resolution, in toluene (60 mL) vinyl acetate (0.9 mL, 9.65 mmol) and PFL (13 mg) were added. The mixture was kept under stirring at room temperature until 41% conversion. The residue, obtained after filtration and evaporation of the solvent, was purified by silica gel column chromatography. By elution with hexane/ethyl acetate 9:1 pure acetate 7 (0.278 g, 40%) was obtained. (R)-alcohol 6 (0.300 g, 50%) was obtained by elution with hexane/ethyl acetate 7:3.

(R)-6 [α]$_D^{20}$+11.8 (c 1 in chloroform). ee>98% (from HPLC)

(R)-7 obtained by acetylation of (R)-6 [α]$_D^{20}$−28.7 (c 1 in chloroform).

Example 7

Isolation of (S)-3-(1'-hydroxy-methyl)-1-tertbutyloxycarbonyl-1,2,3,4-tetrahydroquinoline (compound (S)-6)

First Resolution

The irreversible transterification of (R,S)-6 (1.21 g, 4.6 mmol) was carried out in the same conditions described for the preparation of (R)-6 but the reaction was stopped at 32% conversion. The residue (1.29 g), obtained after usual work-up, was purified by silica gel column chromatography. By elution with hexane/ethyl acetate 9:1 (S)-acetate 7 was recovered as an oil (0.40 g, 29%, 76% ee from HPLC); unreacted (R)-6 was recovered by elution with hexane/ethyl acetate 8:2 as an oil (0.80 g, 65%).

Second Resolution

To a suspension of acetate 7, obtained from the first resolution, (76% ee, 0.310 g, 1 mmol) in phosphate buffer (pH 7, 18 mL), PFL (6 mg) was added. The pH 7 of the mixture was kept in the course of the reaction (5 h) by addition of 0.1 M sodium hydroxide aqueous solution until a calculated 70% conversion. The reaction progress (61%)

was verified by GLC (see above for analysis conditions); the aqueous phase was extracted with dichloromethane (3×15 mL). The collected organic phases were washed with water (2×50 mL) and after usual work-up an oily residue was recovered (0.28 g); purification on silica gel column chromatography afforded pure acetate 7 (0.085 g, 28%, hexane/ethyl acetate 9:1 as eluant) and (S)-alcohol 6 (0.153 g, 58%, hexane/ethyl acetate 8:2 as eluant. (S)-6 showed a >98% ee (by HPLC, eluant: n-hexane/2-propanol 100:2; flow rate 0.250 mL min$^{-1}$).

$[\alpha]_D^{20}$ −12.4 (c 1 in chloroform).

Example 8

Preparation of (R)-3-(1'-hydroxy-methyl)-1-tertbutyloxycarbonyl-1,2,3,4-tetrahydroquinoline, 1'-tosylate (compound (R)-8)

To a solution of (R)-6 (>98% ee, 0.27 g, 1.03 mmol) in pyridine (0.7 mL), cooled in an ice bath, tosyl chloride (0.38 g, 2 mmol) was slowly added. The reaction mixture was kept at room temperature until starting material disappearance (4 h, by TLC hexane/ethyl acetate 7:3). The solution was poured into ice cooled water (5 mL). The precipitate was recovered by suction, washed with water (3×5 mL) and dried at reduced pressure. The recovered tosylate 8 (0.35 g, 82%) was used in the next step without any further purification. $^1$H NMR (CDCl$_3$) δ 1.53 (s, 9H, CH$_3$); 2.39 (m, 1H, H-3), 2.48 (s, 3H, CH$_3$Ar); 2.56 (dd, 1H, H-4); 2.89 (dd, 1H, H-4); 3.34 (dd, 1H, H-2); 3.94 (dd, 1H, H-2); 4.01 (m, 2H, H-4); 7.00 (dd, 1H, H-6); 7.05 (d, 1H, H-5); 7.16 (dd, 1H, H-7); 7.37 (d, 2H, Ar—CH$_3$); 7.63 (d, 1H, H-8); 7.81 (d, 2H, ArSO$_2$).

Example 9

Preparation of (R)-3-methyl-1-tertbutyloxycarbonyl-1,2,3,4-tetrahydroquinoline (compound (R)-9)

To a solution of tosylate (R)-8 (0.35 g, 0.84 mmol) in dry tetrahydrofuran (7 mL) lithium aluminium hydride (0.143 g, 3.77 mmol) was added. The reaction was kept under stirring at room temperature (2 h) until starting material disappearance (by TLC hexane/ethyl acetate 9:1). Water (0.14 ml), 15% sodium hydroxide aqueous solution (0.14 mL) and water (0.42 mL) were sequentially added. The white precipitate was removed by suction on a Celite pad and the filtrate evaporated at reduced pressure affording an oily residue (0.178 g, 86%) that was used in the next step without any further purification. For analytical purposes a sample (50 mg) was purified by silica gel column chromatography. Elution with hexane/ethyl acetate 99:1 afforded pure 9. $^1$H NMR (CDCl$_3$) δ 1.08 (d, 3H, J=7.02 Hz, CH$_3$-1'); 1.55 (s, 9H, CH$_3$); 2.07 (m, 1H, H-3); 2.44 (dd, 1H, H-4); 2.89 (dd, 1H, H-4); 3.12 (dd, 1H, H-2); 3.99 (dd, 1H, H-2); 7.00 (dd, 1H, H-6); 7.08 (d, H-5); 7.15 (dd, 1H, H-7); 7.69 (d, 1H, H-8).

$[\alpha]_D^{20}$ −11.6 (c 1 in chloroform).

IR $v_{max}$ 2973.54, 2928.69, 2873.75, 1694.36, 1491.85, 1366.44, 1152.17 cm$^{-1}$ MS (ESI+) m/z 192.2 [M−C(CH$_3$)$_3$]$^+$, 270.2 [M+Na]$^+$, 517.2 [2M+Na]$^+$.

Example 10

Preparation of (R)-3-methyl-1,2,3,4-tetrahydroquinoline (compound (R)-2)

To a solution of (R)-9 (0.160 g, 0.65 mmol) in dichloromethane (1.5 mL) trifluoroacetic acid (0.26 mL) was added; the solution was kept at room temperature overnight. TLC analysis (hexane/ethyl acetate 8:2) showed a complete conversion. The organic phase was treated with a saturated sodium hydrogen carbonate aqueous solution (2×5 mL) and then washed with water (3×5 mL). After usual work-up the oily residue was purified by silica gel column chromatography. Elution with hexane/ethyl acetate 99:1 afforded pure (R)-2 (0.080 g, 83%) as an oil. The ee (99.4%) was determined by HPLC (hexane/2-propanol 9:1 as eluant; flow rate 0.5 mL R$_t$ (R)-2 15.33, (S)-2 12.99 min. $^1$H NMR (CDCl$_3$) δ 1.08 (d, 3H, H-1'); 2.11 (m, 1H, H-3); 2.46 (dd, 1H, H-4); 2.81 (ddd, 1H, H-4); 2.93 (dd, 1H, H-2); 3.31 (ddd, 1H, H-2); 6.56 (d, 1H, H-5); 6.66 (dd, 1H, H-7); 6.98 (d, 1H, H-8); 7.01 (dd, 1H).

IR $v_{max}$ 3318.07, 2943.52, 2831.70, 1448.90, 1415.85, 1114.99, 1022.01 cm$^{-1}$ MS (ESI+) m/z 148.0 [M+1]$^+$. ms/ms 106.0 [M−CH$_3$CHCH$_2$]$^+$ $[\alpha]_D^{20}$ −73.4 (c 3, in methanol).

The invention claimed is:

1. A process for the preparation of enantiomerically pure (3S)-methyl-1,2,3,4-tetrahydroquinoline comprising the following steps:
   a) transforming quinoline-3-carboxylic acid into a C$_1$-C$_4$ linear or branched alkyl or aryl ester, wherein aryl is a phenyl or benzyl moiety, optionally substituted with one or more C$_1$-C$_4$ linear or branched alkyl groups;
   b) reducing said ester to (R,S)-1,2,3,4-tetrahydroquinoline-3-carboxylate ester;
   c) reducing said (R,S)-1,2,3,4-tetrahydroquinoline-3-carboxylate ester to obtain (R,S)-3-(1'-hydroxy-methyl)-1,2,3,4-tetrahydroquinoline;
   d) protecting the amino group of said (R,S)-3-(1'-hydroxy-methyl)-1,2,3,4-tetrahydroquinoline using di-tertbutyl carbonate to obtain (R,S)-3-(1'-hydroxy-methyl)-1-tertbutyloxycarbonyl-1,2,3,4-tetrahydroquinoline;
   e) reacting the (R,S)-3-(1'-hydroxy-methyl)-1-tertbutyloxycarbonyl-1,2,3,4-tetrahydroquinoline with an ester of vinyl alcohol, the ester comprising a C$_2$-C$_8$, linear or branched alkyl carboxylic acid, in a first transesterification reaction catalyzed by Pseudomonas fluorescens lipase (PFL) in a toluenic solution, wherein the reaction is stopped at a PFL rate of conversion comprised between 30 and 40% to obtain isomer S of (R,S)-3-(1'-carboalkoxy-methyl)-1-tertbutyloxycarbonyl-1,2,3,4-tetrahydroquinoline, which is subsequently hydrolyzed by the PFL at a rate of conversion comprised between 60 and 75% to obtain enantiomerically pure (S)-3-(1'-hydroxy-methyl)-1-tertbutyloxycarbonyl-1,2,3,4-tetrahydroquinoline;
   f) transforming the enantiomerically pure (S)-3-(1'-hydroxy-methyl)-1-tertbutyloxycarbonyl-1,2,3,4-tetrahydroquinoline with a sulphonyl chloride R"—SO$_2$—Cl, wherein R" is a C$_1$-C$_4$ linear or branched alkyl, phenyl, optionally substituted by one or more methyl groups thus obtaining a sulphonyl derivative of (S)-3-(1'-hydroxy-methyl)-1-tertbutyloxycarbonyl-1,2,3,4-tetrahydroquinoline;
   g) reducing said sulphonyl derivative to (S)-3-methyl-1-tertbutyloxycarbonyl-1,2,3,4-tetrahydroquinoline with a hydride; and
   h) removing the protective group of the amino nitrogen atom to obtain enantiomerically pure synthon (S)-3-methyl-1,2,3,4-tetrahydroquinoline.

2. The process according to claim 1, wherein in step a) said ester is methyl ester.

3. The process according to claim 2, wherein in step b) said reduction is a selective hydrogenation with sodium cyanoborohydride.

4. The process according to claim 3, wherein in step c) said reduction of said ester occurs in the presence of a metal hydride.

5. The process according to claim 4, wherein in step e) said vinyl ester is vinyl acetate.

6. The process according to claim 2, wherein in step e) said vinyl ester is vinyl acetate.

7. The process according to claim 1, wherein in step b) said reduction is a selective hydrogenation with sodium cyanoborohydride.

8. The process according to claim 1, wherein in step c) said reduction of said ester occurs in the presence of a metal hydride.

9. The process according to claim 1, wherein in step e) said vinyl ester is vinyl acetate.

10. A process for the preparation of enantiomerically pure (3R)-methyl-1,2,3,4-tetrahydroquinoline comprising the following steps:
   a) transforming quinoline-3-carboxylic acid into a $C_1$-$C_4$ linear or branched alkyl or aryl ester, wherein aryl is a phenyl or benzyl moiety, optionally substituted with one or more $C_1$-$C_4$ linear or branched alkyl groups;
   b) reducing said ester to (R,S)-1,2,3,4-tetrahydroquinoline-3-carboxylate ester;
   c) reducing said (R,S)-1,2,3,4-tetrahydroquinoline-3-carboxylate ester to obtain (R,S)-3-(1'-hydroxy-methyl)-1,2,3,4-tetrahydroquinoline;
   d) protecting the amino group of said (R,S)-3-(1'-hydroxy-methyl)-1,2,3,4-tetrahydroquinoline using di-tertbutyl carbonate to obtain (R,S)-3-(1'-hydroxy-methyl)-1-tertbutyloxycarbonyl-1,2,3,4-tetrahydroquinoline;
   e) reacting the (R,S)-3-(1'-hydroxy-methyl)-1-tertbutyloxycarbonyl-1,2,3,4-tetrahydroquinoline with an ester of vinyl alcohol, the ester comprising a $C_2$-$C_8$, linear or branched alkyl carboxylic acid, in a first transesterification reaction catalyzed by Pseudomonas fluorescens lipase (PFL) in a toluenic solution, wherein the reaction is stopped at a PFL rate of conversion comprised between 55 and 65% to obtain (R)-3-(1'-hydroxy-methyl)-1-tertbutyloxycarbonyl-1,2,3,4-tetrahydroquinoline in a mixture with (S)-3-(1'-carboalkoxy-methyl)-1-tertbutyloxycarbonyl-1,2,3,4-tetrahydroquinoline, and wherein the (R)-3-(1'-hydroxy-methyl)-1-tertbutyloxycarbonyl-1,2,3,4-tetrahydroquinoline is reacted in a second transesterification reaction catalyzed by PFL at a conversion rate between 30 and 45% to obtain enantiomerically pure (R)-3-(1'-hydroxy-methyl)-1-tertbutyloxycarbonyl-1,2,3,4-tetrahydroquinoline;
   f) transforming the enantiomerically pure (R)-3-(1'-hydroxy-methyl)-1-tertbutyloxycarbonyl-1,2,3,4-tetrahydroquinoline with a sulphonyl chloride R"—SO$_2$—Cl, wherein R" is a $C_1$-$C_4$ linear or branched alkyl, phenyl, optionally substituted by one or more methyl groups thus obtaining a sulphonyl derivative of (R)-3-(1'-hydroxy-methyl)-1-tertbutyloxycarbonyl-1,2,3,4-tetrahydroquinoline;
   g) reducing said sulphonyl derivative to (R)-3-methyl-1-tertbutyloxycarbonyl-1,2,3,4-tetrahydroquinoline with a hydride; and
   h) removing the protective group of the amino nitrogen atom to obtain enantiomerically pure synthon (R)-3-methyl-1,2,3,4-tetrahydroquinoline.

11. The process according to claim 10, wherein in step a) said ester is methyl ester.

12. The process according to claim 11, wherein in step b) said reduction is a selective hydrogenation with sodium cyanoborohydride.

13. The process according to claim 12, wherein in step c) said reduction of said ester occurs in the presence of a metal hydride.

14. The process according to claim 13, wherein in step e) said vinyl ester is vinyl acetate.

15. The process according to claim 11, wherein in step e) said vinyl ester is vinyl acetate.

16. The process according to claim 10, wherein in step b) said reduction is a selective hydrogenation with sodium cyanoborohydride.

17. The process according to claim 16, wherein in step c) said reduction of said ester occurs in the presence of a metal hydride.

18. The process according to claim 10, wherein in step c) said reduction of said ester occurs in the presence of a metal hydride.

19. The process according to claim 10, wherein in step e) said vinyl ester is vinyl acetate.

20. Enantiomerically pure (R)-3-methyl-1,2,3,4-tetrahydroquinoline of formula (I):

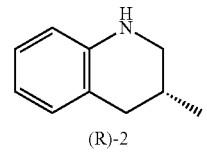

(R)-2

* * * * *

UNITED STATES PATENT AND TRADEMARK OFFICE
CERTIFICATE OF CORRECTION

PATENT NO.       : 9,630,923 B2
APPLICATION NO.  : 14/992226
DATED            : April 25, 2017
INVENTOR(S)      : Grisenti It is certified that error appears in the above-identified patent and that said Letters Patent is hereby corrected as shown below:

On the Title Page

Item (54) should read:
BIOCATALYZED SYNTHESIS OF THE OPTICALLY PURE (R) AND (S) 3-METHYL-1,2,3,4-TETRAHYDROQUINOLINE AND THEIR USE AS CHIRAL SYNTHONS FOR THE PREPARATION OF THE ANTITHROMBOTIC (21R)- AND (21S)-ARGATROBAN Item (57) ABSTRACT should read:
The present invention relates to the biocatalyzed synthesis of enantiomerically pure (3R) and (3S)-methyl-1,2,3,4-tetrahydroquinoline. Said enantiomerically pure compounds are useful as chiral synthons in organic synthesis and, in particular, for the preparation of diastereomerically pure (21R) and (21S)-agratroban and its analogues. New compounds used as intermediates in the process of the invention are also disclosed.

Signed and Sealed this
Eighth Day of August, 2017

Joseph Matal
*Performing the Functions and Duties of the
Under Secretary of Commerce for Intellectual Property and
Director of the United States Patent and Trademark Office*